(12) United States Patent
Vorsa et al.

(10) Patent No.: US 7,270,837 B2
(45) Date of Patent: Sep. 18, 2007

(54) ANTI-INFLAMMATORY CRANBERRY FLAVONOL EXTRACT PREPARATIONS

(75) Inventors: Nicholi Vorsa, Atco, NJ (US); Irina O. Vvedenskaya, Edison, NJ (US); Mou-Tuan Huang, Englewood Cliffs, NJ (US); Robert T Rosen, deceased, late of Monroe Township, NJ (US); by Sharon L. Rosen, legal representative, Monroe Township, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 83 days.

(21) Appl. No.: 10/985,471

(22) Filed: Nov. 10, 2004

(65) Prior Publication Data

US 2006/0088610 A1 Apr. 27, 2006

Related U.S. Application Data

(60) Provisional application No. 60/518,294, filed on Nov. 10, 2003.

(51) Int. Cl.
*A61K 36/45* (2006.01)
(52) U.S. Cl. .................................................... 424/732
(58) Field of Classification Search ...................... None
See application file for complete search history.

(56) References Cited

U.S. PATENT DOCUMENTS

| 5,474,774 | A | * | 12/1995 | Walker et al. | ............... | 424/732 |
| 5,525,341 | A |   | 6/1996  | Walker et al. | | |
| 5,646,178 | A | * | 7/1997  | Walker et al. | ............... | 514/456 |
| 5,650,432 | A |   | 7/1997  | Walker et al. | | |
| 6,210,681 | B1 |  | 4/2001  | Walker et al. | | |
| 6,440,471 | B2 |  | 8/2002  | Walker et al. | | |
| 6,608,102 | B1 |  | 8/2003  | Walker et al. | | |
| 2001/0051191 | A1 | * | 12/2001 | Katske | ...................... | 424/733 |

OTHER PUBLICATIONS

1984. Sobota. Inhibition of Bacterial adherence by cranberry juice: potential use for the treatment of urinary tract infections. The journal of Urology. vol. 131.*
1994. Food phytochemicals for cancer prevention I. ACS Symposium series vol. 546. Chapter 1. pp. 2-15.□□.*
2000. Wang et al. Antioxidative and cytotoxic components of highbush blueberry. Phytochemicals and phytopharmaceuticals. pp. 271-277.*
2001. Huang et al. Inhibitory effect of an extract of the root of the chinese plant polygonum cuspidatum on chemically-induced several biomarker changes and tumorigenesis in mice. Abstract of Papers. 221st ACS national meeting.*
1994. Ho et al. ACS symposium series, vol. 547: food phytochemicals for cancer prevention II. Teas spices and herbs.*
1999. Jin et al. Flavonoid glycodises from ledum palustre I. subsp. decumbens hulton. Daru. vol. 7. No. 4,1999. pp. 5-8.*
irishhealth.com.*
Cunningham et al., 2002 "Analysis and Standardization of Cranberry Products. In Quality Management of Nutraceuticals", Eds. Ho, C., and Zheng, Q.Y. ACS, Washington D.C. ACS Symposium Series 803, 152-167..
Foo et al., 2000 The Structure of Cranberry Proanthocyanidins Which Inhibit Adherence of Uropathogenic P-Fimbriated *Escherichia coli* in vitro. *Phytochemistry*, 5:173-181.
Foo et al., 2000, "A-Type Proanthocyanidin Trimers from Cranberry That Inhibit Adherence of Uropathogenic P-Fimbriated *Escherichia coli*.", *J. Nat Prod.*, 63:1225-1228.
Formica et al., 1995, "Review of the Biology of Quercetin and Related Bioflavonoids," *Fd. Chem. Toxic.* 33; 1061-1080.
Hong et al., 1986, "Cranberry Juice Composition.", J. Assoc. Off. Anal. Chem., 69:199-207.
Mabry et al., 1970, "The Systematic Identification of Flavonoids", Springer-Verlag: New York, 128-130.
Vvedenskaya et al., 2004, "Characterizaiton of Flavonols in Cranberry (Vaccinium macrocarpon) Powder", *J. Agric. Food Chem.*, 52(2):188-195.
Marwan et al., 1982, "Identification of the Hydroxycinnamic Acid Derivatives in Cranberries", *J. Food Sci.*, 47:774-782.
Puski and Francis, 1967, "Flavonol Glycosides in Cranberries", *J. Food Sci* , 32:527-530.
Sobota, 1984, "Inhibition of Bacterial Adherence by Cranberry Juice: Potential Use for the Treatment of Urinary Tract Infections", *J. Virol.*, 131:1013-1016.
Yan et al., 2002, "Antioxidant Activities and Antitumor Screening of Extracts from Cranberry Fruit (Vaccinium Macrocarpon)", *J. Agric. Food Chem.*, 50:5844-5849.

* cited by examiner

*Primary Examiner*—Christopher R. Tate
*Assistant Examiner*—Melenie McCormick
(74) *Attorney, Agent, or Firm*—Jones Day

(57) ABSTRACT

The present invention is directed to extracts of cranberries (*Vaccinium macrocarpon*) comprising either mixed flavonols that are substantially free of anthocyanins and proanthocyanidins or a purified cranberry flavonol compound, including myricetin-3-β-xylopyranoside, quercetin-3-β-glucoside, quercetin-3-α-arabinopyranoside, 3'-methoxyquercetin-3-α-xylopyranoside, quercetin-3-O-(6"-p-coumaroyl)-β-galactoside, and quercetin-3-O-(6"-benzoyl)-β-galactoside. The present invention also embodies the use of those extracts, as well as extracts comprising the cranberry flavonol compound quercetin-3-α-arabinofuranoside, for the treatment of inflammatory disorders. Pharmaceutical, food, dietary supplement, and cosmetic compositions utilizing the extracts or compounds of the present invention are also recited.

24 Claims, 10 Drawing Sheets

Table 1. Retention Times, Relative Peak Areas, $\lambda_{max}$, m/z values of $[M+H]^+$, $[M-H]^-$ and Fragment Ions of Flavonoid Constituents Resolved by HPLC of 60% Methanol Fraction 1.

| Peak | Retention time (min) | Relative peak area, % | $\lambda_{max}$, nm | $[M-H]^-$ and fragment ions in APCI MS | $[M+H]^+$ in ESI MS | Structure |
|---|---|---|---|---|---|---|
| 1 | 29.0 | 8.3 | 261.5 356.5 | 479 (25%), 317 (100%) | nd | Myricetin-3-β-galactoside[1] |
| 2 | 29.8 | 0.9 | 261.5 356.5 | 449 (100%), 317 (90%) | 451 | Myricetin-3-α-xylopyranoside[3] |
| 3 | 32.0 | 2.2 | 233.2 266.2 294.4 356.5 | nd | nd | nd |
| 4 | 32.5 | 3.6 | 261.5 356.5 | 449 (65%), 317 (100%) | nd | Myricetin-3-α-arabinofuranoside[1,2] |
| 5 | 34.3 | 21.5 | 256.8 356.5 | 463 (55%), 301 (100%) | 465 | Quercetin-3-β-galactoside[1,2] |
| 6 | 35.1 | 0.9 | 256.8 356.5 | 463 (60%), 301 (100%) | 465 | Quercetin-3-β-glucoside[3] |
| 7 | 35.8 | 1.3 | 256.8 356.5 | nd | nd | nd |
| 8 | 36.3 | 8.2 | 256.8 356.5 | 433 (45%), 301 (100%) | nd | Quercetin-3-α-xylopyranoside[1] |
| 9 | 37.6 | 6.7 | 256.8 356.5 | 433 (35%), 301 (100%) | 435 | Quercetin-3-α-arabinopyranoside[3] |
| 10 | 39.8 | 9.7 | 256.8 356.5 | 433 (35%), 301 (100%) | 435 | Quercetin-3-α-arabinofuranoside[1,2] |
| 11 | 40.4 | 14.3 | 256.8 351.7 | 447 (55%), 301 (100%) | nd | Quercetin-3-rhamnopyranoside[1,2] |
| 12 | 41.2 | 1.6 | 256.8 356.5 | 477 (100%), 315 (25%) | nd | 3'-methoxyquercetin-3-β-galactoside[1] |
| 13 | 41.7 | 3.9 | 256.8 356.5 | 507(100%), 463(48%), 345(48%), 331(46%) | nd | Dimethoxymyricetin-hexoside Methoxymyricetin-pentoside |
| 14 | 42.9 | 0.6 | 256.8 356.5 | 447 (100%), 315 (55%) | nd | Methoxyquercetin-pentoside |
| 15 | 43.3 | 2.3 | 256.8 356.5 | 447 (100%), 315 (32%) | nd | 3'-methoxyquercetin-3-α-xylopyranoside[3] |
| 16 | 44.0 | 4.6 | 256.8 351.7 256.8 318.4 351.7sh | 609 (35%), 447 (70%), 315 (25%), 301 (100%) | 611[4] | Methoxyquercetin-pentoside; Quercetin-3-O-(6''-p-coumaroyl)-β-galactoside[3] (Compound 16a) |
| 17 | 44.5 | 0.8 | 256.8 356.5 | nd | nd | nd |
| 18 | 44.8 | 1.5 | 256.8 313.6 356.5 | nd | nd | nd |
| 19 | 45.6 | 5.6 | 256.8 356.5 | 567 (100%), 301 (52%) | 569 | Quercetin-3-O-(6''-benzoyl)-β-galactoside[3] |
| 20 | 46.2 | 0.1 | 256.8 356.5 | nd | nd | nd |
| 21 | 46.8 | 0.3 | 256.8 356.5 | 581(53%), 431(100%), 299(28%) | nd | Methoxykaempferol derivative |
| 22 | 47.4 | 1.1 | 256.8 290sh 364.6 | 593(50%), 431(100%), 345(68%), 299(75%) | nd | Methoxykaempferol derivative |

Note: nd – not determined; [1] – compounds not previously identified in cranberry; [4] – $[M+H]^+$ for peak 16a.

Table 2. $^1$H and $^{13}$C NMR shifts of Cranberry Flavonol Glycosides (Parts per Million)

| Position | 2 | | 5 | | 6 | | 9 | | 10 | | 15 | | 16a | | 19 | |
|---|---|---|---|---|---|---|---|---|---|---|---|---|---|---|---|---|
| | $^{13}$C | $^1$H | $^{13}$C | $^1$H | $^{13}$C | $^1$H | $^{13}$C | $^1$H | $^{13}$C | $^1$H | $^{13}$C | $^1$H | $^{13}$C | $^1$H | $^{13}$C | $^1$H |
| 6 | 99.5 | 6.15 | 99.4 | 6.04 | 100.4 | 6.06 | 99.6 | 6.14 | 99.5 | 6.14 | 94.6 | 6.14 | 99.8 | 6.41 | 99.4 | 6.13 |
| 8 | 94.1 | 6.32 | 94.8 | 6.23 | 95.5 | 6.27 | 94.5 | 6.35 | 94.3 | 6.35 | 89.7 | 6.39 | 94.6 | 6.54 | 94.0 | 6.29 |
| 2' | 109.1 | 7.12 | 117.1 | 7.59 | 116.8 | 7.50 | 116.8 | 7.47 | 116.1 | 7.43 | 108.6 | 7.71 | 117.0 | 7.84 | 116.5 | 7.45 |
| 5' | | | 116.1 | 6.79 | 116.1 | 6.81 | 116.1 | 6.80 | 116.2 | 6.79 | 111.0 | 6.82 | 116.4 | 7.05 | 115.8 | 6.77 |
| 6' | 109.1 | 7.12 | 122.7 | 7.39 | 122.7 | 7.44 | 122.7 | 7.60 | 122.4 | 7.50 | 118.2 | 7.46 | 122.7 | 7.85 | 122.8 | 7.58 |
| 1" | 102.5 | 5.31 | 103.1 | 4.97 | 102.2 | 5.06 | 102.3 | 5.22 | 108.6 | 5.53 | 97.5 | 5.20 | 102.9 | 5.66 | 101.9 | 5.45 |
| 2" | 74.3 | 3.34 | 71.8 | 3.59 | 74.3 | 3.26 | 71.7 | 3.73 | 83.0 | 4.11 | 69.5 | 3.17 | 71.8 | 3.58 | 72.1 | 3.58 |
| 3" | 77.0 | 3.14 | 73.3 | 3.43 | 76.2 | 3.25 | 72.6 | 3.48 | 77.6 | 3.67 | 71.3 | 3.14 | 73.9 | 3.41 | 74.4 | 3.42 |
| 4" | 70.2 | 3.31 | 68.6 | 3.69 | 69.9 | 3.15 | 66.9 | 3.62 | 86.8 | 3.51 | 65.1 | 3.21 | 69.1 | 3.64 | 69.3 | 3.68 |
| 5" | 66.9 | 2.91/ 3.60 | 75.8 | 3.36 | 77.1 | 3.06 | 65.2 | 3.18/ 3.57 | 61.6 | 3.25 | 61.7 | 3.54/ 2.89 | 73.8 | 3.66 | 74.2 | 3.75 |
| 6" | | | 60.9 | 3.34/ 3.44 | 61.1 | 3.34/ 3.47 | | | | | | | 64.3 | 4.26/ 4.35 | 64.9 | 4.23 |

Table 3. Inhibitory effect of cranberry fractions after Sephadex LH-20 column chromatography on TPA-induced edema of mouse ears. Weight data are expressed as the mean of 8 ear punches.

| TREATMENT | WEIGHT OF EAR PUNCHES (mg / Ear) | MEAN SEPARATION (SNK multiple means test, $P \leq 0.05$) | % INHIBITION |
|---|---|---|---|
| Acetone + Acetone | 7.4 | e | - |
| Acetone + TPA | 12.4 | a | - |
| Cranberry, 60% MeOH (166 μg) + TPA | 10.7 | b | 34.3 |
| Cranberry, 60% MeOH (500 μg) + TPA | 8.5 | c d e | 78.6 |
| Cranberry, 100% MeOH (166 μg) + TPA | 10.2 | b c | 45.3 |
| Cranberry, 100% MeOH (500 μg) + TPA | 9.8 | b c d | 53.3 |
| Cranberry, 70% Acetone (166 μg) + TPA | 8.6 | c d e | 77.0 |
| Cranberry, 70% Acetone (500 μg) + TPA | 8.1 | d e | 85.5 |
| Curcumin (95 μg) + TPA | 8.5 | c d e | 79.0 |

Table 4. Inhibitory effect of quercetin-3-*O*-(6"-benzoyl)-β-galactoside (Cranberry peak 19) on TPA-induced edema of mouse ears. Weight data are expressed as the mean of 10 ear punches (12 punches for Acetone + TPA treatment.) ± the standard error.

| TREATMENT | NUMBER OF MICE PER GROUP | WEIGHT OF EAR PUNCHES (mg / Ear) | % INHIBITION |
|---|---|---|---|
| Acetone + Acetone | 5 | 7.57 ± 0.13 | - |
| Acetone + TPA | 6 | 16.12 ± 0.64 | - |
| Cranberry Peak 19 (87.5 μg) + TPA | 5 | 13.21 ± 0.77 | 34.0 |
| Cranberry Peak 19 (175 μg) + TPA | 5 | 11.41 ± 0.54 | 55.1 |
| Curcumin (135 μg) + TPA | 5 | 11.22 ± 0.77 | 57.3 |

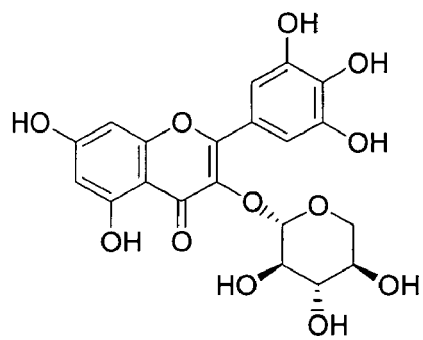
2
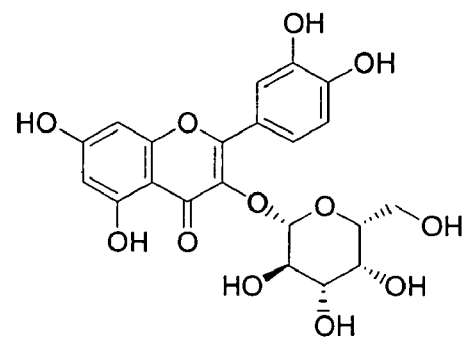
5
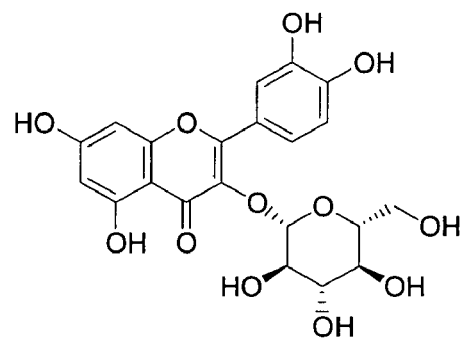
6
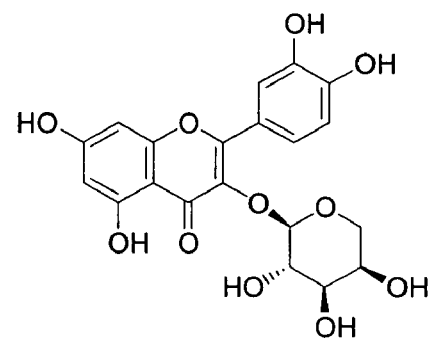
9
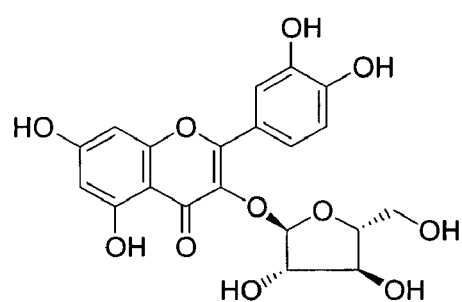
10
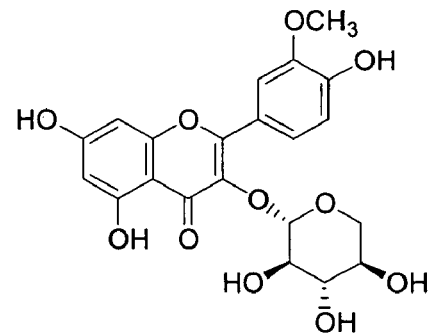
15
Figure 4. (Continued on the following page.)

16a

19

ANTI-INFLAMMATORY CRANBERRY FLAVONOL EXTRACT PREPARATIONS

CROSS REFERENCE TO RELATED APPLICATIONS

The present application claims priority under 35 USC § 119(e) to U.S. Provisional Application Ser. No. 60/518,294, filed on Nov. 10, 2003, which is incorporated by reference in its entirety herein.

FIELD OF THE INVENTION

The present invention is directed to extracts of cranberries (*Vaccinium macrocarpon*) comprising either mixed flavonols that are substantially free of anthocyanins and proanthocyanidins or a purified cranberry flavonol compound, including myricetin-3-β-xylopyranoside, quercetin-3-β-glucoside, quercetin-3-α-arabinopyranoside, 3'-methoxyquercetin-3-α-xylopyranoside, quercetin-3-O-(6"-p-coumaroyl)-β-galactoside, and quercetin-3-O-(6"-benzoyl)-β-galactoside. The present invention also embodies the use of those extracts, as well as extracts comprising the cranberry flavonol compound quercetin-3-α-arabinofuranoside, for the treatment of inflammatory disorders, particularly irritation of the urinary tract due to both bacterial and non-bacterial causes.

BACKGROUND OF THE INVENTION

Millions of women are diagnosed with urinary tract infections each year. Countless numbers of dogs and cats also suffer from chronic urinary infections and die from renal infections. *E. coli* is the most common pathogen associated with these infections, causing over 80% of urinary tract infections. Over 30% of women suffer recurrent infections within a 6 to 12-month period and are forced to resort to extended use of antibiotics to treat these infections. Recurrent use of antibiotics can lead to pathogen resistance and result in deleterious side effects and toxicity reactions. Consequently there exists a need for safe alternative medications (e.g., non-antibiotics) that can be used to prevent or treat urinary tract infections in both animals and humans. Moreover, urinary tract inflammation is a painful and often debilitating symptom of bacterial infection as well as many diseases of both known and unknown etiology. Thus, there is currently a need for new treatments to effectively mitigate the pain arising from inflammation of the urinary tract.

The two main forms of urinary tract infection are the renal infection known as pyelonephritis and the bladder infection referred to as bacterial cystitis. As the bladder is closer to the anus, the site of entry for bacteria giving rise to urinary tract infections, cystitis is far more common than pyelonephritis. Moreover, although cystitis is not as deadly as its renal counterpart, it is associated with pervasive inflammation giving rise to severe bladder pain as well as frequent, urgent, and painful urination. Cystitis is also often a recurrent condition, resulting in long term and often debilitating discomfort for those afflicted.

Unfortunately, the causes of the battery of adverse conditions affecting the urinary tract are only partially understood. Thus, inflammatory conditions of the bladder of both known and unknown etiology are commonly referred to as cystitis. As noted above, cystitis may be bacterial in nature, arising from infection of the bladder by *E. coli*, Cystitis may also embody urinary tract inflammation due to a number of non-bacterial sources, for example, allergic responses to food or insufficient water intake, which allows the bladder and urethral tissues to become dry, thus leading to deposition of crystallized uric acid on the tissues and associated irritation. Interstitial cystitis is a recurrent condition of uncertain etiology. It is a source of frustration for both doctors and patients alike, as it has no apparent infective cause and is frequently debilitating. Indeed, according to the first epidemiological study of interstitial cystitis in the U.S. (Held, et al. 1990), 50% of patients could not maintain full-time employment due to the painful effects of the disease.

Treatments for cystitis include antimicrobials, anti-inflammatory agents, buffering agents, muscle relaxants, mast cell stabilizers, painkillers including tricyclic antidepressants and transcutaneous electrical nerve stimulator (TENS) units, catheterization and intravesicular instillation of heparin, the anti-inflammatory agent dimethyl sulfoxide, the detergent sodium oxychlorosene, the caustic agent silver nitrate, or chromolyn sodium, and surgical techniques. Unfortunately, many of these treatments are themselves painful, and many are also unsuitable for personal treatment in the home.

The fruit of the American cranberry (*Vaccinium macrocarpon*) has received considerable attention for its putative human health benefits. Most of the focus is on the flavonoid constituents due to their relatively high biological activity in various assays. In vitro chemical assays have rated cranberries as having some of the highest antioxidant values of over 21 fruits (Vinson et al. 2001; Sun et al. 2002), and the overall phenolic content appears to correlate with the level of antioxidant activity. The 'Folin-Ciocalteu' colorimetric test has found cranberry to have one of the highest phenolic contents of a number of fruit species tested (Vinson et al. 2001; Sun et al. 2002). The phenolic classes identified in cranberry include phenolic acids (Marwan et al. 1982; Heimhuber et al. 1990; Zheng et al. 2000; Zuo et al. 2002), anthocyanins (Hong et al. 1986; Hong et al. 1990), flavonols (Puski et al. 1967; Yan et al. 2002), and flavan-3-ols, which consist of both monomers and the polymer classes procyanidins and proanthocyanidins (Foo et al. 1981; Foo et al. 2000a; Foo et al. 2000b; Cunningham et al. 2002). As described more fully below, we have previously identified cranberry A-type proanthocyanidins as possessing anti-adherence activities against uropathogenic type P *E. coli* (Foo et al. 2000a; Foo et al. 2000b; U.S. Pat. No. 6,608,102).

Cranberry juice has been shown to reduce bacteriuria associated with urinary tract infections in humans (Avorn et al. 1994). One mechanism implicated in yielding this beneficial effect is the ability of certain compounds present in cranberries to inhibit the adhesion of type 1 and type P fimbriated *E. coli* to human epithelial cells (Sobota 1984; Schmidt et al. 1988; Zafriri et al. 1989). Type P fimbriated *E. coli* have been implicated as the main cause of pyelonephritis, while type 1 fimbriated *E. coli* are the predominant causative agent of bacterial cystitis.

Zafriri et al. (1989) reported that fructose present in cranberry juice inhibited the adherence of type 1 *E. coli* to uroepithelial cells, and that cranberry juice also contained one or more non-dialyzable substances that inhibited binding of type P *E. coli* but failed to define the chemical nature of those substances.

U.S. Pat. Nos. 5,474,774, 5,525,341, and 5,646,178 to Walker et al. disclose cranberry extracts having the ability to inhibit the adherence of *E. coli* to uroepithelial cells. This activity was obtained by extracting whole cranberries with acidified alcohol followed by separation of the activity from simple sugars by precipitation with a metal acetate or sulfate. Upon further manipulation, the reported activity consisted of a fraction enriched in polyphenol and flavonoid compounds that contained as much as 10% anthocyanins. The specificity of this anti-adherence activity for type 1 or type P *E. coli* was, however, not determined.

WO 96/30033 and U.S. Pat. Nos. 5,646,178 and 5,650,432 to Walker et al. disclose a series of proanthocyanidin monomers, dimers, and polymers as well as flavonoid derivatives thereof and related compounds purported to have the ability to interfere with bacterial adherence to a surface. The dimers and polymers of Walker were limited to compounds having B-type interflavanoid linkages. However, Walker failed to provide any experimental data correlating biological activity with a specifically identified compound. The extraction method involved alkalinizing a plant material homogenate to a pH greater than 10 (a treatment which causes degradation of proanthocyanidins) and precipitating the polyphenolic compounds (together with other materials) by addition of alcohol. This precipitate contained the proposed anti-adherence activity and was further fractionated to yield the purified active compound. Using this process with an aqueous solution of commercially available Ocean Spray cranberry powder, Walker reported obtaining a single active compound and partially characterized the compound but failed to provide its chemical structure. The Walker assay methods could not distinguish between anti-adherence activities with respect to type 1 or type P *E. coli*, thus Walker was also unable to characterize the biological activity of this compound.

Commonly assigned U.S. Pat. No. 6,608,102 to Howell et al. discloses plant proanthocyanidin extracts that are substantially free of anthocyanins and flavonols and specifically inhibit the adherence of type P *E. coli* to epithelial cells. The Howell '102 patent represents the culmination of our work that conclusively demonstrated that proanthocyanidins are the chemical agents in cranberries and other plants that are responsible for this anti-adherence activity, and that proanthocyanidins having at least one A-type interflavanoid linkage are particularly potent agents for this activity. Later U.S. Pat. Nos. 6,210,681 and 6,440,471 to Walker et al. disclose similar proanthocyanidin extracts.

Thus, we have previously determined that proanthocyanidins present in cranberries exhibit anti-adherence activity with respect to the binding of uroepithelial cells solely by type P fimbriated *E. coli*, However, as bladder infections are associated with type 1 fimbriated *E. coli*, the anti-adherence activity of these compounds is ineffective for the treatment of bacterial cystitis. Although fructose in cranberry juice has been found to possess an analogous anti-adherence activity with respect to the binding of type 1 fimbriated *E. coli* to uroepithelial cells and is therefore theoretically effective at hindering bladder infections, this discovery was made well over a decade ago, yet there remains a substantial need for efficacious treatments for cystitis.

Cranberries and cranberry products have been used in the treatment of urinary tract infections both alone and in conjunction with other therapies. The basis for such treatments has traditionally implicated the antimicrobial properties associated with cranberries. Originally, this antimicrobial activity was thought to arise from acidification of the urine due to the intake of cranberry juice, resulting in an unfavorable environment for bacterial survival. Later, the focus shifted to the bacterial anti-adherence activity of fructose and proanthocyanidins that has been elucidated in the aforementioned literature. For example, Cystopurin, a Roche product for the treatment of cystitis that is available in the UK, incorporates a cranberry juice extract as an adjunctive therapy in a potassium citrate buffer designed to alleviate painful urination by neutralizing urinary acidity. However, as noted above, the only constituent of cranberries known to possess anti-adherence activity against the type 1 fimbriated *E. coli* commonly involved in bacterial cystitis is fructose. Moreover, inflammation of the urinary tract may also arise from non-bacterial sources, in which case such anti-adherence activities are therapeutically ineffective. Finally, individuals having non-bacterial cystitis must exercise care in the process of self-medication with cranberry products, as, depending on the nature of the preparation, acids and other bladder irritants may be present that could result in aggravation of the inflammatory condition.

After bacterial adherence, internalization of type 1 *E. coli* by bladder epithelial cells represents another potential target for the treatment of bacterial cystitis. Traditional thinking had considered uropathogenic *E. coli* to exist as extracellular pathogens within the urinary tract, despite the fact that transmission electron microscopy studies of infected rat and mouse bladders indicated that bladder epithelial cells could internalize the pathogens in vivo (Fukushi et al. 1979; Mc Taggart et al. 1990). Although such internalization was initially regarded as a host defense mechanism, Mulvey et al. (1998) suggested that it inured beneficially to the survival of the bacteria. Specifically, they determined that type 1 *E. coli* induced programmed cell death and exfoliation of bladder epithelial cells, however, pathogens could avoid expulsion by such mechanisms by invading into deeper tissue. They also speculated that the frequency of recurrence of infection despite antibiotic treatment could be linked to the persistence of bacteria within the cells of the bladder long after the death of extracellular pathogens by such treatments. This speculation was later confirmed by their discovery that a persistent reservoir of *E. coli* could be established by bacterial invasion of bladder epithelial cells, followed by intracellular replication and reemergence of the pathogens (Mulvey et al. 2001). Upon reemergence, the pathogens evade clearance via exfoliation of the infected bladder cells by anchoring themselves and invading into deeper, healthy cells that become exposed to the bladder lumen as a result of the exfoliation of cells from more superficial layers. These internalized pathogens can persist in a latent state and, as the result of an as yet undetermined trigger, reemerge to cause recurrent infections.

Martinez et al. (2000) reported that the FimH element, an adhesin located on the tip of the type 1 pilus, mediates the bacterial invasion of human bladder epithelial cells. Specifically, they determined that the FimH element induces rearrangements of the host cell cytoskeleton resulting in a zippering effect by which the host cell engulfs the pathogen. Martinez also reported that these cytoskeletal rearrangements required protein tyrosine phosphorylation and phosphoinositide 3-kinase activation, and that a quercetin derivative, LY294002 (Vlahos et al. 1994), was a potent inhibitor of both of these activities and effectively inhibited type 1 pilus-mediated bacterial invasion of bladder epithelial cells in urinary tract infections. Tyrosine kinase inhibitors, including both quercetin and myricetin, directly inhibit enzymes such as the hexose transporter GLUT1 via specific competition for the ATP binding site (Vera et al. 2001). Myricetin has been found to be the most potent flavonol for inhibiting transport of methylglucose and deoxyglucose, while isorhamnetin (3'-methoxyquercetin) was the most potent at inhibiting transport of dehydroascorbic acid (Vera et al. 2001).

Quercetin has attracted much attention for its potential health benefits, and has been associated with numerous biological activities, including anti-inflammatory activities (Formica et al. 1995). Quercetin and related compounds inhibit a number of the processes associated with inflammation including lipopolysaccharide induced production of nitric oxide and tumor necrosis factor a (TNF-α) (Kawada et al. 1998; Wadsworth et al. 1999) and cytokine production (Xagorari et al. 2001). The invasion of bladder cells by type 1 *E. coli* has been shown to induce cytokine production by a lipopolysaccharide dependent mechanism (Schilling et al. 2001). Among fruit species, the cranberry contains one of the highest concentrations of quercetin, ranging from 11 to 25 mg/100 g of fresh fruit (Bilyk et al. 1986; Hakkinen et al. 1999). Quercetin is predominantly found in a conjugated form with various sugars, and the sugar moiety may significantly influence its bioavailability and adsorption (Hollman et al. 1995; Hollman et al. 1999; Wofffram et al. 2002).

Quercetin has been used in the treatment of inflammatory conditions associated with the urinary tract. U.S. patent application Ser. Nos. 757358 and 848187 to Katske, et al. disclose compositions and methods for the treatment of non-bacterial prostatitis and non-bacterial cystitis, respectively. These compositions comprise bioflavonoids having a substantial percentage of quercetin that exhibit both antioxidative and anti-inflammatory properties and a digestive enzyme such as bromelin or papain to increase the intestinal absorption of the bioflavonoid component. The compositions are directed towards treating the pain associated with cystitis and prostatitis by an anti-inflammatory mechanism. However, substances such as papain are allergenic to many individuals, and these enzymes have caustic and corrosive effects on the digestive mucous membranes.

Thus, there is presently a need for non-antibiotic treatments for urinary tract infections. There is also a need for a generalized therapy for cystitis, whether bacterial or non-bacterial in origin, that is innocuous and can be used for self-medication in the home. Accordingly, applicants have discovered that the cranberry flavonol compositions of the present invention advantageously possess superior anti-inflammatory activity. These compositions are amenable to use in the treatment of inflammatory disorders, particularly those of the urinary tract arising from both bacterial and non-bacterial sources. Moreover, these compositions can be formulated to contain one or more flavonols that can inhibit the invasion of uroepithelial cells by type 1 fimbriated *E. coli*, Advantageously, these compositions are also free from irritants of the bladder as well as the digestive mucous membranes. Thus, the cranberry flavonol compositions of the present invention embody natural, innocuous treatments that can be used beneficially for self-medication by those afflicted with inflammatory conditions of the urinary tract generally, and cystitis particularly. The cranberry flavonol compositions of the present invention are effective for and amenable to the treatment of such inflammatory conditions regardless of whether such conditions originate from bacterial or non-bacterial sources.

SUMMARY OF THE INVENTION

The present invention is directed to cranberry flavonol extracts that are substantially free of anthocyanins and proanthocyanidins. These flavonol extracts have marked anti-inflammatory activity, and are thus useful in the treatment of inflammatory conditions generally, and particularly in the treatment of urinary tract inflammation. The invention also provides a method of obtaining these flavonol extracts from cranberries (*Vaccinium macrocarpon*). The present invention is also directed to purified cranberry flavonol compounds, including quercetin-3-O-(6"-benzoyl)-β-galactoside, which we have found to possess marked anti-inflammatory activity, as well as methods to obtain these compounds from cranberries. Additionally, the present invention embodies a processing method to increase the yield of quercetin-3-O-(6"-benzoyl)-β-galactoside in cranberry powder. Finally, the invention relates to methods of preventing or treating inflammatory conditions, particularly urinary tract inflammation from either bacterial or non-bacterial sources, in a mammal by administering a composition comprising a flavonol extract of cranberries or a cranberry flavonol compound such as quercetin-3-O-(6"-benzoyl)-β-galactoside to the mammal in an amount and for a time sufficient to prevent, reduce or eliminate inflammation and thereby lead to an amelioration or curing of the condition. Preferably the mammal undergoing treatment is a human, but the method is also applicable to animals, especially domesticated animals, such as cats and dogs, and livestock.

Pharmaceutical compositions are provided which comprise a flavonol composition, including pharmaceutically acceptable salts of any of the flavonol compounds, and a pharmaceutically acceptable carrier. Also provided are pharmaceutical compositions comprising at least one cranberry flavonol compound, such as quercetin-3-O-(6"-benzoyl)-β-galactoside, including pharmaceutically acceptable salts thereof, and a pharmaceutically acceptable carrier. In some instances, it may be preferable to provide the therapeutic dosage in the form of a food additive in a beverage such as a cranberry juice-based beverage containing additional flavonols or quercetin-3-O-(6"-benzoyl)-β-galactoside. The invention also provides food and dietary supplement compositions comprising a flavonol composition or at least one cranberry flavonol compound, such as quercetin-3-O-(6"-benzoyl)-β-galactoside, including pharmaceutically acceptable salts of any of these compounds, mixed with a consumable carrier. Consumable carriers include, but are not limited to, livestock feed, domestic animal feed and consumable food products, especially cranberry containing food products, and are defined more fully in the detailed description of the invention herein. Finally, the present invention also provides cosmetic compositions incorporating the active agents disclosed herein. These pharmaceutical, food, dietary supplement, and cosmetic compositions are useful to prevent or treat inflammatory conditions generally, and particularly urinary tract inflammation, and more particularly cystitis.

BRIEF DESCRIPTION OF THE DRAWINGS

Table 1 provides chromatographic and mass spectral data for individual components of Fraction 1 of the 60% methanol eluate from Sephadex LH-20 chromatography of cranberry extract.

Table 2 provides NMR data for eight components of Fraction 1 of the 60% methanol eluate from Sephadex LH-20 chromatography of cranberry extract.

Table 3 provides data on the inhibitory effect of cranberry fractions from Sephadex LH-20 chromatography on TPA-induced edema of mouse ears.

Table 4 provides data on the inhibitory effect of quercetin-3-O-(6"-benzoyl)-β-galactoside (Cranberry peak 19 from Fraction 1 of the 60% methanol eluate from Sephadex LH-20 chromatography) on TPA-induced edema of mouse ears.

Figure 1:
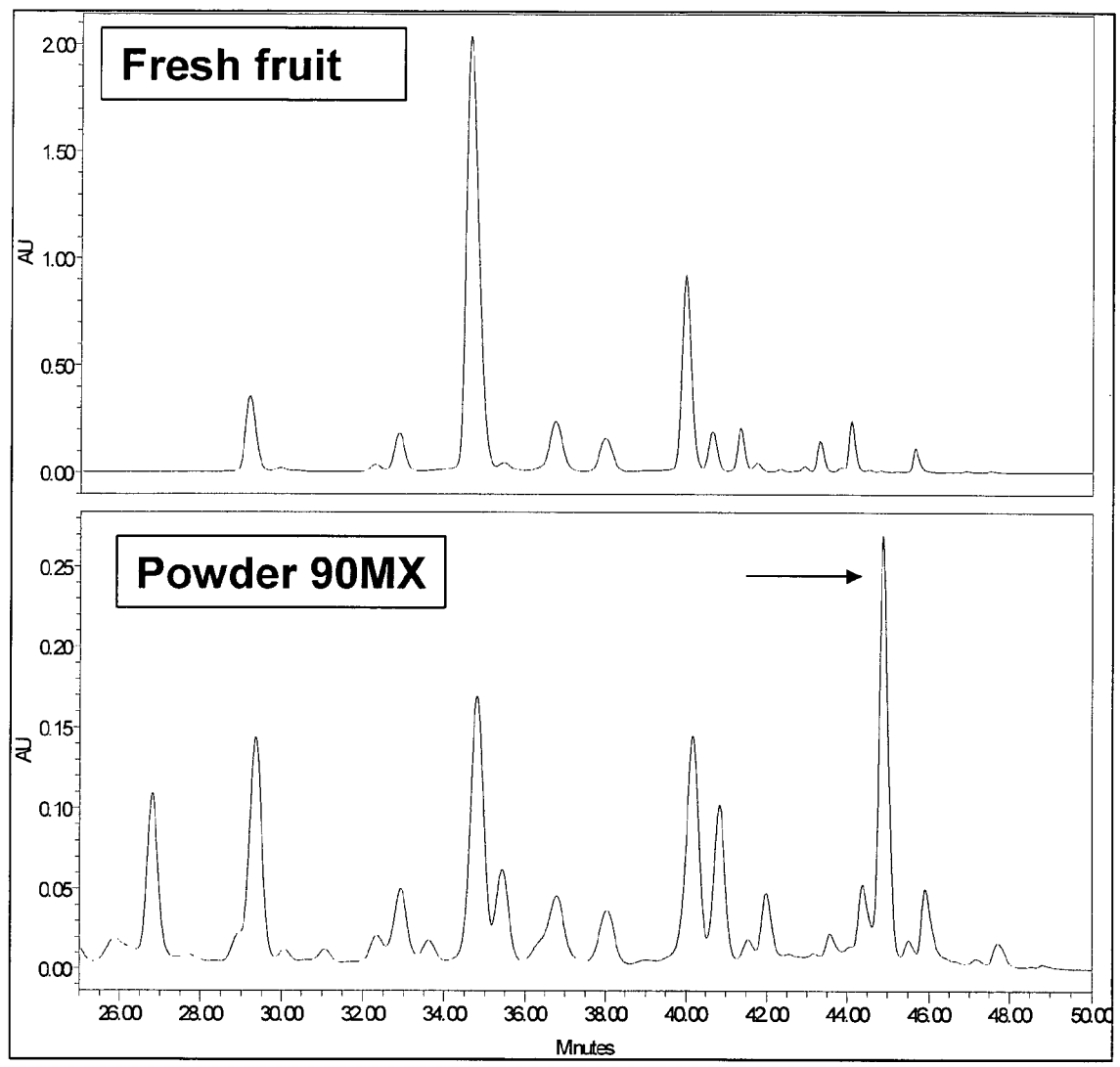

FIG. 1 shows HPLC chromatograms of the flavonol glycosides extracted from fresh cranberries (60% methanol Fraction 1 after Sephadex LH-20 column chromatography) and a cranberry solids powder (90 MX) showing an increase in the concentration of the compound corresponding to Peak 19 (having retention time of approximately 45 minutes) upon processing to form the cranberry solids powder, under the following chromatographic conditions: Sorbax SB-C18 250 mm×4.6 mm i.d. column; eluate, 2% formic acid in methanol; flow rate, 1 ml min$^{-1}$; absorbance, 340 nm.

Figure 2:
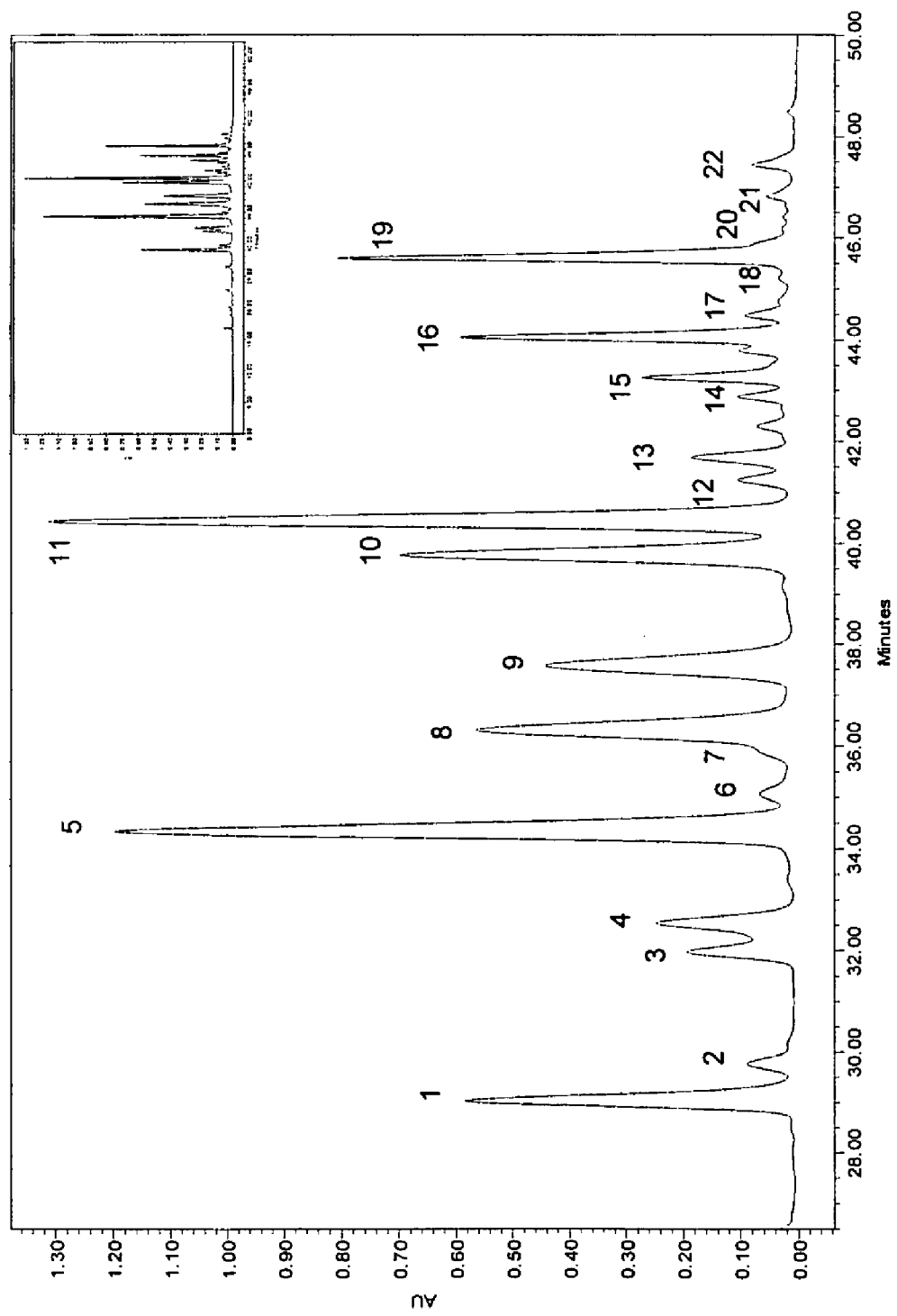

FIG. 2 is the HPLC chromatogram of Fraction 1 of the 60% methanol eluate from Sephadex LH-20 chromatography, with peaks numbered corresponding to the compound numbers presented in Table 2, under the following chromatographic conditions: Sorbax SB-C18 250 mm×4.6 mm i.d. column; eluate, 2% formic acid in methanol; flow rate, 1 ml min$^{-1}$; absorbance, 340 nm.

Figure 3:
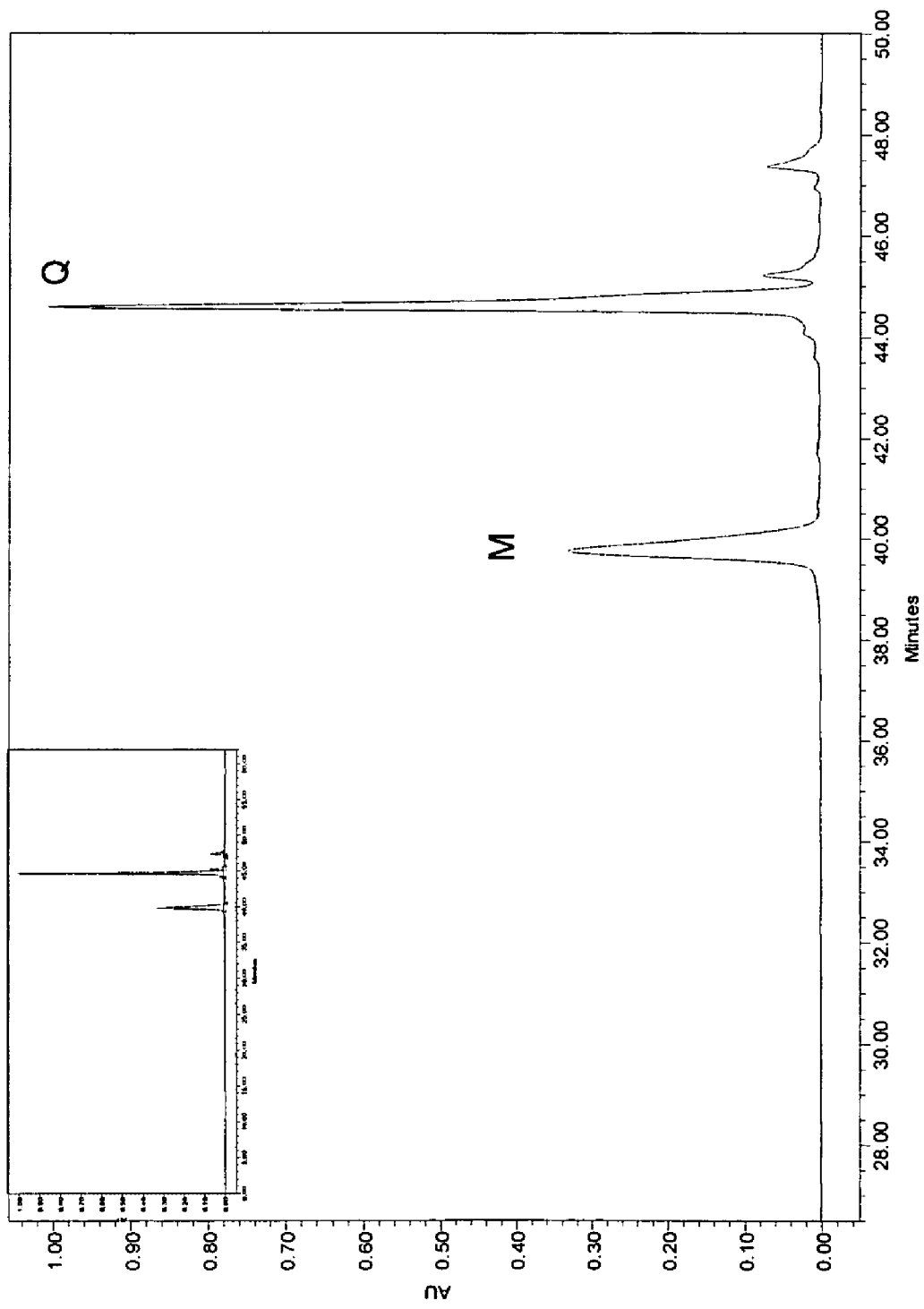

FIG. 3 is the HPLC chromatogram of Fraction 2 of the 60% methanol eluate from Sephadex LH-20 chromatography under the following chromatographic conditions: Sorbax SB-C18 250 mm×4.6 mm i.d. column; eluate, 2% formic acid in methanol; flow rate, 1 ml min$^{-1}$; absorbance, 340 nm, wherein the peak labeled M is myricetin and the peak labeled Q is quercetin.

Figure 4:
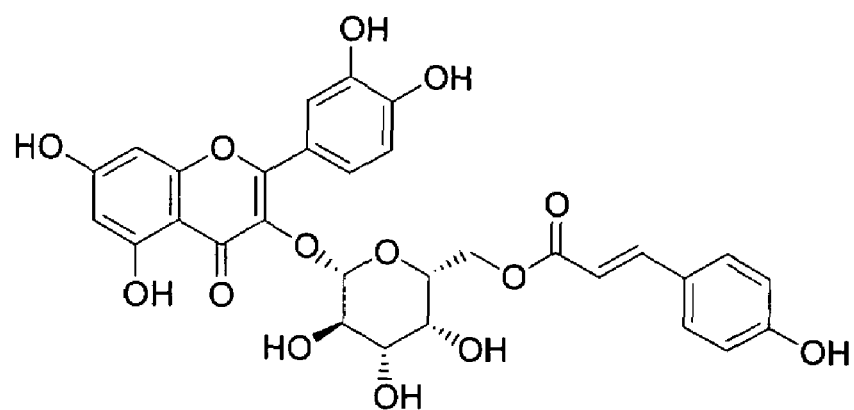
Figure 4:
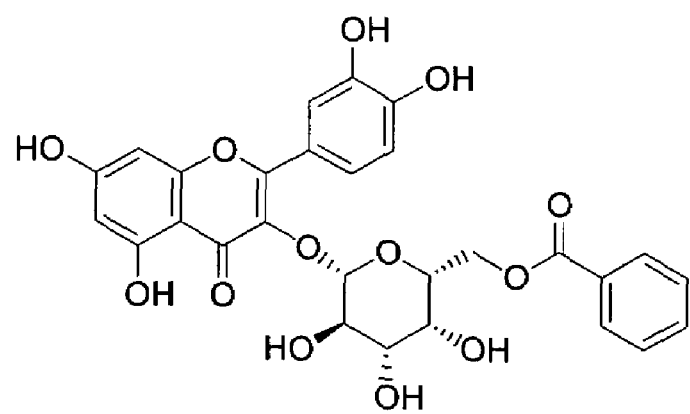

FIG. 4 shows the chemical structures of eight flavonol glycosides isolated from Fraction 1 of the 60% methanol eluate from Sephadex LH-20 chromatography, specifically: myricetin-3-β-xylopyranoside (2), quercetin-3-β-galactoside (5), quercetin-3-β-glucoside (6), quercetin-3-α-arabinopyranoside (9), quercetin-3-α-arabinofuranoside (10), 3'-methoxyquercetin-3-α-xylopyranoside (15), quercetin-3-O-(6"-p-coumaroyl)-β-galactoside (16a), and quercetin-3-O-(6"-benzoyl)-β-galactoside (19).

Figure 5:
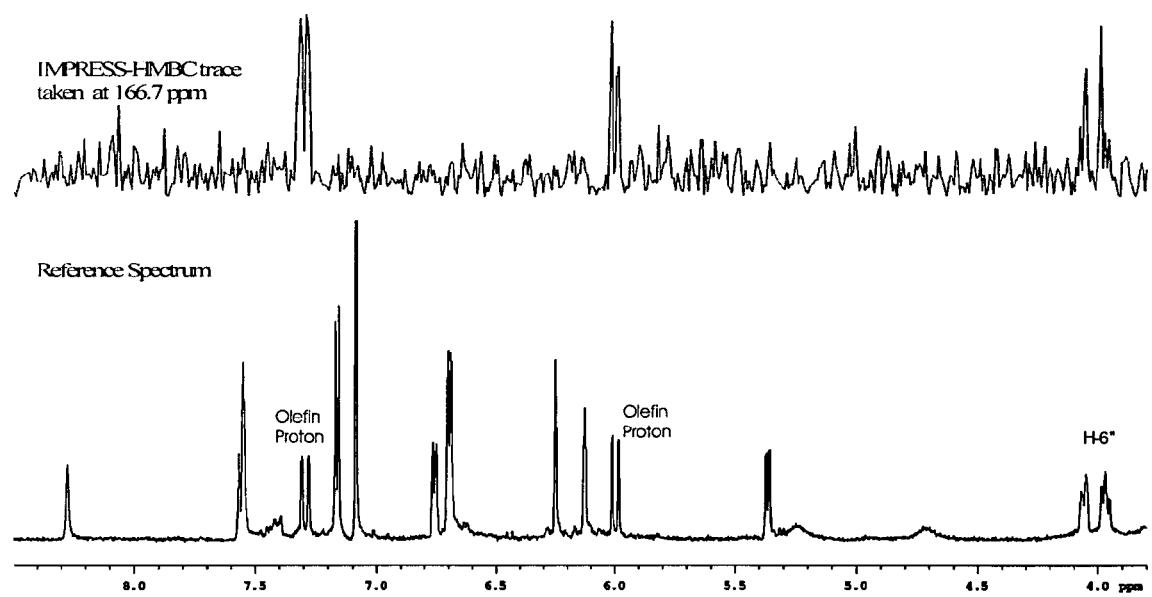

FIG. 5 shows the proton NMR spectrum (bottom) of Cranberry peak 16a from Fraction 1 of the 60% methanol eluate from Sephadex LH-20 chromatography and the trace extracted from the 6 Hz optimized IMPRESS-HMBC data set at 166.7 ppm showing 2- and 3-bond coupling responses from the olefin protons of the coumaroyl moiety and the galactose C-6" protons to the same ester carbonyl resonance.

DETAILED DESCRIPTION OF THE INVENTION

We have characterized the flavonol glycosides in spray-dried cranberry powder and have isolated a cranberry extract containing mixed flavonols that is substantially free of both anthocyanins and proanthocyanidins. This extract exhibits a high degree of anti-inflammatory activity in the TPA-induced mouse ear edema assay and is rich in glycosylated quercetin derivatives. We have also isolated and characterized six flavonols not previously reported in cranberry, including the novel compound quercetin-3-O-(6"-benzoyl)-β-galactoside, which we have found to be a potent anti-inflammatory agent in the TPA-induced mouse ear edema assay. Interestingly, we have also discovered that this compound is more abundant in processed cranberry powder than in the fresh fruit itself (FIG. 1), and thus have determined means to generate the purified compound in high yield.

The cranberry flavonol extracts and compounds of the present invention can be used in various food, dietary supplement, pharmaceutical, and cosmetic formulations for the treatment and prevention of inflammatory conditions generally. Moreover, as many of the extracts are both rich in glycosylated quercetin derivatives and free from bladder irritants, they can be used advantageously for the treatment and prevention of cystitis arising from either bacterial or non-bacterial origins. An "inflammatory condition" is defined herein as any condition or disease in which inflammation is either symptomatic or plays a prominent role in the condition or disease, including but not limited to: urinary tract infection and/or inflammation, osteoarthritis, rheumatoid arthritis, cardiovascular diseases, dermatitis, cancer, diabetes, obesity, asthma, multiple sclerosis, and other diseases in which inflammation is involved.

Compositions comprising the extracts or compounds of the present invention can be formulated for administration as foods or dietary supplements using one or more consumable carriers. A "consumable carrier" is herein defined as any food, food ingredient, or food additive, or any excipient utilized for tabletting, encapsulation, or other formulation of an active agent for oral administration, whether for human or animal use. Specific additives are well known to those of skill and are listed in places such as the U.S. Pharmacopeia. For dietary supplements, the extract can be mixed according to methods routine in the art. Dietary supplements can be prepared in a variety of forms including, but not limited to, liquid, powder, or solid pill forms. In the present invention, the active agents can be administered either alone or in combination with other phytochemicals where combining compounds or extracts would lead to synergistic effects. Examples of other phytochemicals which can be used in combination with the active agents of the present invention include, but are not limited to, resveratrol and its hydroxylated and methoxylated analogs, rosemary extract, green tea extracts, orange peel extracts, Mexican Bamboo, and Huzhang extracts. The active agents of the present invention can also be added directly to foods and ingested as part of a normal meal. Various methods are known to those skilled in the art for addition or incorporation of such agents into foods.

Alternatively, compositions comprising these extracts can be administered as conventional pharmaceuticals using one or more physiologically acceptable carriers or excipients, referred to herein as "pharmaceutically acceptable carriers." Pharmaceutical compositions can be formulated for administration by any route including, but not limited to, inhalation or insufflation (through mouth or nose), oral, buccal, parenteral, topical, vaginal, or rectal administration. The active agents of the present invention can be applied topically to treat and prevent inflammatory conditions in either pharmaceutical or cosmetic applications. Compositions for use in the present invention can also be administered in the form of tablets or capsules prepared by conventional means with pharmaceutically acceptable excipients such as binding agents, fillers, lubricants, disintegrants, or wetting agents. Examples of specific compounds for use in formulating tablets and capsules are described in detail in the U.S. Pharmacopeia. Tablets comprising the extract can also be coated by methods well known in the art. Liquid preparations for oral administration can also be used. Liquid preparations can be in the form of solutions, syrups or suspensions, or a dry product for reconstitution with water or another suitable vehicle before use. Such liquid preparations can be prepared by conventional means with pharmaceutically acceptable additives such as suspending agents, emulsifying agents, non-aqueous vehicles, and preservatives. Again, specific additives are well known to those of skill and are listed in places such as the U.S. Pharmacopeia. The compositions of the present invention can be formulated to provide controlled time release of the active agents. For buccal administration the extract can be formulated as a tablet or lozenge.

For administration by inhalation, compositions for use in the present invention can be delivered in the form of an aerosol spray in a pressurized package or as a nebulizer, with use of suitable propellants. In the case of a pressurized aerosol, the dosage unit can be determined by providing a valve to deliver a metered dose. For rectal administration or vaginal administration, compositions for use in of the present invention can be formulated as suppositories, creams, gels, or retention enemas.

Parenterally administered compositions are formulated to allow for injection, either as a bolus or as a continuous infusion. Formulations for injection can be prepared in unit dosage forms, such as ampules, or in multi-dose units, with added preservatives. The compositions for injection can be in the form of suspensions, solutions, or emulsions, in either oily or aqueous vehicles. They may also contain formulatory agents such as suspending agents, stabilizing agents, and/or dispersing agents. The active ingredient may also be presented in powder form for reconstitution with a suitable vehicle before use. Specific examples of formulating agents for parenteral injection are found in the U.S. Pharmacopeia.

Freeze dried cranberry powder extracted with 80% aqueous acetone followed by ethyl acetate yielded a phenolic fraction with a high degree of anti-inflammatory activity in the TPA-induced mouse ear edema assay. In order to optimize the resolution of compounds within the main phenolic classes (phenolic acids, anthocyanins, flavonols, and proanthocyanidins), we assayed a number of analytical C18 reverse-phase columns, eluates and gradients to determine which of these combinations provided the best HPLC profile. As a result, we determined that upon Sephadex LH-20 column chromatography of the ethyl acetate extract with successive volumes of water, 60% aqueous methanol (v/v) (collected in two fractions referred to herein as Fraction 1 and Fraction 2), 100% methanol, and 70% aqueous acetone (v/v) to separate the cranberry components generally into the main phenolic classes, HPLC separation of these eluates on a Zorbax SB-C18 reversed phase column with a binary solvent system (Solvent A, 2% aqueous formic acid; Solvent B, 2% formic acid in methanol) and gradient elution (Linear gradient of 5-25% B from 0 to 5 min, linear gradient of 25-40% B from 5 to 25 min, isocratic elution with 40% B from 25 to 30 min, linear gradient of 40-95% B from 30 to 45 min, and isocratic elution with 95% B from 45 to 50 min) provides optimal simultaneous resolution of cranberry phenolic acids, anthocyanins and flavonols.

After Sephadex LH-20 column chromatography of the ethyl acetate extract, we assayed the 60% methanol (Fraction 1 and Fraction 2 combined), 100% methanol, and 70% acetone eluates for anti-inflammatory activity via the TPA-induced mouse ear edema assay as described in Example 2 herein. Of these three, the 60% methanol eluate exhibited a significant dose response effect in reducing the weight of mouse ear edema by 34.3% and 78.6% at 166 µg and 500 µg, respectively, as compared to the estimated mean inflammation of the acetone and TPA control. HPLC analysis with PDA detection indicated this fraction was composed primarily of phenolics with maximum absorbance near 350-360 nm. We determined that Fraction 1 of the 60% methanol eluate consisted of flavonol glycosides, while the later-eluting Fraction 2 consisted of flavonol aglycones, predominantly myricetin and quercetin. Further isolation and determination of the components was undertaken as described herein. As expected, the 70% acetone eluate tested positive for proanthocyanidins with the HCl-vanillin assay.

Assay of Fraction 1 of the 60% methanol eluate using the chromatographic method according to the present invention afforded 22 peaks in contrast to the 9 reported previously in cranberry (Yan et al. 2002) (FIG. 2). Additionally, the method of the present invention is more effective for the separation of individual flavonol glycosides within this class of flavonoids. The increased resolution provided by our method enabled us to identify additional flavonoids, six of which were structurally determined. Two of these newly identified compounds, 16a and 19, are very rare acylated quercetin-galactosides. Quercetin-3-O-(6"-p-coumaroyl)-β-galactoside (16a) has only been reported in *Ledum palustre* L. (Jin et al. 1999). We have isolated quercetin-3-O-(6"-benzoyl)-β-galactoside (19) for the first time from a natural source. The increased resolution provided by our method enables the isolation of individual flavonol glycosides or aglycones present in cranberries and thus also the preparation of bioactive compositions incorporating one or more of these compounds.

Using the analytical methods of the present invention, we discovered some distinct differences between the flavonol glycoside profiles of processed cranberry powder and fresh cranberries, the most pronounced of which were the elevated contents of myricetin, quercetin, and quercetin-3-O-(6"-benzoyl)-β-galactoside after processing. Specifically, we evaluated the content of the latter compound in extracts of three commercial cranberry cultivars (Stevens, Ben Lear, and Early Black) and four samples of processed cranberry powder. We consequently determined that this component rose from an average of 1.27% (Range 0.16-2.28%) of the total flavonol fraction in fresh fruit to 3.44% (Range 2.50-4.02%) in processed powder extracts, as shown in FIG. 1. As described in Example 3 below, we found this compound to be a highly effective inhibitor of inflammation in the TPA-induced mouse ear edema assay. Thus, our invention also embodies a method for obtaining this compound in high yield by isolating the compound from processed cranberry preparations. Such processing entails the concentration of cranberry juice by means known to those of skill in the art, including but not limited to heating at atmospheric pressure or under vacuum, freeze drying, or a combination of these to obtain a cranberry preparation having a high solids content.

The invention is illustrated more fully by the following non-limiting Examples. Moreover, applicants' article "Characterization of Flavonols in Cranberry (*Vaccinium macrocarpon*) Powder" *J. Agric. Food Chem*. 2004, 52, 188-195 is incorporated by reference in its entirety herein.

EXAMPLE 1

Isolation and Characterization of Flavonol Glycosides and Aglycones from Cranberry Powder Reagents All reagents were purchased from Fisher Scientific (Pa.) and Sigma (Mo.) and were of analytical or HPLC grade. Dimethylsulfoxide (DMSO)-$d_6$ (99.96% D) was obtained from Cambridge Isotope Laboratories (Mass.). Standards of quercetin-3-galactoside, quercetin-3-glucoside, quercetin-3-rhamnoside, quercetin, myricetin and kaempferol were purchased from INDOFINE Chemical Company, Inc. (N.J.). Sephadex™ LH-20 for column chromatography was obtained from Amersham Pharmacia Biotech AB (Sweden).

Extraction and Fractionation of Flavonoids

Flavonoids from 1.0 kg of freeze dried cranberry powder 90-MX supplied by Ocean Spray Cranberries, Inc., (Mass.) were extracted twice with 80% acetone/water (v/v) (1:10), filtered and partially evaporated under reduced pressure at 35° C. to remove the acetone. The resultant aqueous phase was defatted by extraction with hexane (1:1) and the aqueous layer was further extracted with three portions of ethyl acetate (1:1). After concentration in vacuo, the pooled ethyl acetate fraction (24.8 g) was further fractionated using column chromatography. A portion of ethyl acetate extract (8.0 g) was dissolved in 60% methanol and loaded onto the 100×50 mm column packed with hydrated Sephadex LH-20, Subsequent elution with water, 60% methanol/water (v/v), 100% methanol and 70% acetone/water (v/v) was applied to fractionate phenolic classes and remove all phenolic constituents from the column. Fractions eluted were monitored by analytical HPLC and tested for anti-inflammatory activity as described below. The 60% methanol fraction contained mostly constituents with maximum absorbance at 340 nm and was eluted from the column in two sequential 1200 ml volumes, yielding 660 mg (Fraction 1) and 600 mg (Fraction 2) of phenolics. Fraction 1 was used for the further isolation of individual constituents by preparative HPLC as described below. Final purification of the compound 16a was achieved on a Sephadex LH-20 column (20×40 mm) using methanol as the eluting solvent.

HPLC Apparatus and Chromatographic Conditions

Analytical HPLC

HPLC analysis was performed on a Waters Millenium HPLC system composed of a Water In-line Degasser, a Waters 600E Multisolvent Delivery System, a Waters 717 plus Autosampler, and a Waters 996 photodiode array detector. A Zorbax SB-C18 250 mm×4.6 mm i.d. (5 μm) reversed phase column protected with a Waters Guard-Pak Precolumn Module was used for analysis. Separations were carried out in a binary solvent system: solvent A, 2% formic acid; solvent B, 2% formic acid in methanol. A program of a linear gradient 5-25% B from 0 to 5 min, 25-40% B from 5 to 25 min, an isocratic elution with 40% B from 25 to 30 min, a linear gradient 40-95% B from 30 to 45 min and an isocratic elution with 95% B from 45 to 50 min at flow rate of 1 mL/min was used. PDA detection was used to monitor the eluate from 210 to 700 nm.

Preparative HPLC

A Zorbax SB-C18 250 mm×21.2 mm i.d. (5 μm) column was used with the binary solvent system and gradient elution as described in the preceding section and a flow rate of 15 mL/min. The column effluents were monitored from 210 to 400 nm. Fractions were collected using a Waters Fraction Collector II. A gradient elution program afforded the collection of eight individual compounds that were purified by re-chromatography under the same conditions.

Identification of Cranberry Flavonol Glycosides and Aglycones

Individual constituents of the flavonol extract according to the present invention were identified by comparison of chromatographic retention time and UV spectral characteristics with standards, as well as by MS and NMR techniques.

Comparison with Standards

Standard curves for identification of flavonols were prepared using authentic standards dissolved in methanol at a concentration of 1 mg/ml and stored at −20° C. as stock solutions. Identification of quercetin-3-galactoside, quercetin-3-glucoside, quercetin-3-rhamnoside, myricetin and quercetin was performed by matching their retention time and spectral characteristics measured at 340 nm against those of standards.

Mass Spectrometry

Atmospheric pressure chemical ionization (APCI) mass spectrometry in the negative-ion detection mode was obtained on a VG Platform mass spectrometer (Micromass, Manchester, U.K.). A Zorbax SB-C18 250×4.6 mm reversed-phase column and the methanol/formic acid/water mobile phase described above were used with a flow rate of 1 ml/min. Typical tuning parameters were as follows: corona, 3 kV; high voltage lens, 0.0 kV; cone 15 V; source temperature, 150° C.; and APCI probe temperature, 450° C. Spectra were scanned over a mass range of m/z 150-1100 at 1.0 s per cycle.

Positive-ion electrospray ionization (ESI) mass spectrometry was acquired on a ThermoFinnigan TSQ-Quantum mass spectrometer using standard operating parameters. A Zorbax Eclipse XDB C18 150×4.6 mm reversed-phase column and a binary solvent gradient of A (water/acetonitrile/trifluoroacetic acid (TFA) 95:5:0.025) and B (water/acetonitrile/TFA 5:95:0.025) were used. Spectra were scanned over a mass range of m/z 190-800 at 1.0 s per cycle.

NMR Spectroscopy

The NMR data were obtained on either a Varian INOVA three-channel NMR spectrometer operating at a $^1$H observation frequency of 599.730 MHz and equipped with a 3 mm Nalorac Z•SPEC MIDTG gradient inverse triple resonance NMR probe or a Varian INOVA three-channel NMR spectrometer operating at a $^1$H observation frequency of 499.792 MHz and equipped with a 5 mm Varian Chili-probe® gradient inverse triple resonance NMR probe operating at a coil temperature of 25° K. The sample temperature was regulated at 20° C. for all samples except peak 9, for which data were acquired at 32° C. Samples were dissolved in ~150 μL of DMSO-$d_6$ and transferred to a Wilmad 3 mm NMR tube for analysis. Peak 16a was dissolved in ~150 μL of 90:10 DMSO-$d_6$:benzene-$d_6$. Chemical shifts were referenced relative to the residual solvent resonances at 2.49 and 39.5 ppm for $^1$H and $^{13}$C, respectively. All $^1$H NMR data were acquired with a spectral width of 16 ppm. Correlated Spectroscopy (COSY) data were acquired as 256 increments with 8 transients per increment; squared sinebell apodization was used in both dimensions. Heteronuclear Single Quantum Coherence (HSQC) and Heteronuclear Single Quantum Coherence Total Correlation Spectroscopy (HSQCTOCSY) data were acquired as 96 increments with 24 and 96 transients per increment, respectively. Both data sets had an F1 spectral window of 146 ppm and were apodized with a gaussian weighing function in both dimensions; the HSQC-TOCSY mixing time was set to 18 ms. Heteronuclear Multiple Bond Correlation (HMBC) data were acquired as 96 increments with 320 transients per increment. The F1 spectral width was 241 ppm. Squared sinebell apodization was used in both dimensions.

Results

Chromatography

FIG. 2 shows the chromatogram of Fraction 1 of the 60% methanol eluate from Sephadex LH-20 column chromatography, while FIG. 3 shows the corresponding chromatogram of Fraction 2 of the 60% methanol eluate. Both chromatograms were acquired using UV absorbance detection at 340 nm. Fraction 1 exhibits well-resolved flavonoid peaks at $R_t$ 29-48 min and includes some minor constituents of $R_t$ 15-26 min. Fraction 2 exhibits four peaks, two of which ($R_t$ 39.4, 44.6) are predominant.

All peaks on the Fraction 1 chromatogram having retention time between 29 and 48 min, peaks numbered from 1 to 22 as shown, display absorbance profiles corresponding to those of flavonols (Mabry et al. 1970; Machiex et al. 1990). Three peaks of $R_t$ 34.3, 35.1 and 40.4 min were found to be consistent with retention times and UV-visible spectra of standards quercetin-3-galactoside (5), quercetin-3-glucoside (6) and quercetin-3-rhamnoside (11), respectively (FIG. 2, Table 1). The two major flavonoids that eluted in Fraction 2 (FIG. 3) were identified as myricetin ($R_t$ 39.8) and quercetin ($R_t$ 44.6).

Mass Spectrometry

APCI LC-MS analysis in the negative-ion mode was used to identify the molecular weights of constituents eluting in 60% methanol Fraction 1 and to ascertain whether they were sugar conjugates as evidenced by loss of 162/132 mass units from the pseudomolecular ion. The results obtained are summarized in Table 1 together with spectral characteristics, distribution of peaks by area percentages (at 340 nm) and retention time under chromatographic conditions employed. APCI LC-MS of phenolics gives intense deprotonated molecular ions [M-H]$^-$ in the negative-ion mode.

Peak 1 exhibited an intense [M-H]$^-$ ion peak at m/z 479 and a fragment ion at m/z 317 [M-$C_6H_{11}O_5$]$^-$ corresponding to a myricetin-hexoside. The spectrum of the peaks 2 and 4 both gave [M-H]$^-$ ion peaks at m/z 449 and a fragment ion at m/z 317 [M-$C_5H_9O_4$]$^-$ consistent with myricetin-pentoside conjugates. Peaks 5 and 6 exhibited in the APCI mass spectra characteristic [M-H]$^-$ ions at m/z 463 and fragment ions at m/z 301 [M-$C_6H_{11}O_5$]$^-$ corresponding to quercetin hexosides. These peaks, when compared with chromatographic behavior and UV-visible spectra of standards, were identified as quercetin-3-β-galactoside and quercetin-3-β-glucoside, respectively.

Three peaks of $R_t$ 36.3, 37.6, and 39.8 (8,9,10) showed intense [M-H]$^-$ ion peaks at m/z 433 and fragment ions at m/z 301 [M-$C_5H_9O_4$]$^-$ consistent with quercetin-pentoside structures. The exact nature of the sugar moiety cannot be ascertained by LC-MS. The spectra released for peak 11 exhibited a [M-H]$^-$ ion at m/z 447 and a fragment ion at m/z 301 [M-$C_6H_{11}O_4$]$^-$ which corresponds to quercetin-3-α-rhamnoside as determined by comparison with a standard.

Peak 12 gave a [M-H]$^-$ ion peak at m/z 477 with a fragment ion at m/z 315 [M-$C_6H_{11}O_5$]$^-$ consistent with a possible structure containing a monomethoxyquercetin-hexoside. The position of the methyl substituent could not be determined. Peaks 14 and 15 exhibited [M-H]$^-$ ions at m/z 447 and had fragment ions at m/z 315 [M-$C_5H_9O_4$]$^-$ corresponding to possible methoxylated quercetin-pentosides. The MS spectra of peaks 13, 16, 21 and 22 appear more complex and suggest the presence of a mixture of components. Possible constituents of these peaks correspond to monomethoxymyricetin-pentoside (m/z 463, 331) and dimethoxymyricetin-hexoside (m/z 507, 345) for peak 13 and to derivatives of methoxykaempferol (m/z 299) for peaks 21 and 22. Deprotonated molecular ions for peak 16 indicate the possible presence of a monomethoxyquercetin-pentoside (m/z 447, 315) and an acylated derivative of quercetin-hexoside (m/z 609, 301).

One of the latest eluting peaks at $R_t$ 45.6, peak 19, gave [M-H]$^-$ and fragment ion peaks at m/z 567 and 301 which we initially speculated to be a quercetin-hexose ester with benzoic acid. Peak 19 was subsequently confirmed to be quercetin-3-O-(6"-benzoyl)-β-galactoside by NMR spectroscopy.

NMR Spectroscopy

For structural determination of various flavonoid constituents by NMR spectroscopy, Fraction 1 of the 60% methanol eluate was further fractionated by preparative HPLC. The two step procedure applied for the elution of constituents with 60% methanol during Sephadex LH-20 column chromatography was useful to prevent the coelution of the abundant simple flavonols myricetin and quercetin with the peaks corresponding to flavonol conjugates (FIGS. 1 and 2).

The NMR analysis of purified peaks was supported by ESI LC-MS data performed in the positive-ion mode (Table 1).

Sufficient amounts of eight pure components (2, 5, 6, 9, 10, 15, 16, 19) were obtained. These compounds were conclusively identified by NMR as myricetin-3-β-xylopyranoside (2), quercetin-3-β-galactoside (5), quercetin-3-β-glucoside (6), quercetin-3-α-arabinopyranoside (9), quercetin-3-α-arabinofuranoside (10), 3'-methoxyquercetin-3-α-xylopyranoside (15), and quercetin-3-O-(6"-benzoyl)-β-galactoside (19) (FIG. 4). Peak 16 represented a mixture of coeluting compounds, and was subjected to additional purification on a Sephadex LH-20 column with 60% methanol as the eluting solvent. The compound with [M-H]$^-$ ion peak at m/z 609 (16a) was used for structural determination by NMR spectroscopy, and determined to be quercetin-3-O-(6"-p-coumaroyl)-β-galactoside (FIG. 4).

The previous identification of peaks 5 and 6 as quercetin-3-β-galactoside and quercetin-3-β-glucoside, respectively, were confirmed by NMR data (Table 2). For peak 6, the anomeric proton appeared as a doublet (J=7.6 Hz) while the 2", 3", and 4" proton resonances appeared as triplets (J=7.8–8.8 Hz), consistent with a glucose moiety. The flavonoid at $R_t$ 39.8 (peak 10) was identified as quercetin-3-α-arabinofuranoside, which is consistent with previously reported data (Puski et al. 1967; Yan et al. 2002). Quercetin-3-β-glucoside (6) and structures 2, 9, 15, 16a, and 19 represent compounds not yet reported in cranberry or cranberry products.

Myricetin-3-β-xyloside (2) in the pyranose form was apparent due to the 4" carbon chemical shift and the strongly anisochronous 5" methylene responses which are consistent with those of a pentose in the pyranose form. The anomeric signal appeared as a J=7.43 Hz doublet, and taken along with the downfield shift of the carbon resonance, indicates a β-configuration. The 3" proton resonance is an apparent triplet (J=8.66 Hz), establishing a trans-diaxial relationship for the 2"-3" and 3"-4" pairs.

The pyranose form of quercetin-3-α-arabinoside (9) was indicated by the 4" carbon chemical shift and the anisochronous 5" methylene group. The anomeric signal appeared as a J=5.2 Hz doublet at 5.22/102.3 ppm, implying the α-configuration. The 2"-3" coupling constant of J=6.7 Hz indicated a trans-diaxial configuration, while 3"-4" coupling constant (J=3.1 Hz) implies an axial-equatorial orientation, yielding the assignment of arabinopyranose. Thus, the relatively major flavonol quercetin-3-arabinoside exists in two sugar forms, as a pyranose (~6.7%) and the previously reported (10) furanose form (~9.7%) (Table 1).

Peak 15 presented NMR spectra indicative of the quercetin backbone and a xylopyranose sugar moiety. An aromatic methoxy resonance was also observed (3.71, 51.9 ppm) that yielded a 3-bond HMBC response to the 3' carbon resonance at ~144 ppm, allowing assignment of the site of the methoxy substitution.

A quercetin backbone was observed in the isolate of peak 16a by NMR spectroscopy, and resonances consistent with the presence of a galactopyranose sugar moiety were observed. Two new AB spin systems were observed in the downfield region; one integrating for a total of two protons (7.58/145/5 and 6.29/114.6 ppm), the other integrating for four protons (7.46/130.9 and 6.99/116.7 ppm). The larger set of resonances was readily assigned as a 1,4-substituted aromatic system based on HMBC data, while the smaller system was assigned as a trans-olefin due to its 15.9 Hz coupling constant. An IMPRESS-HMBC data set was used to establish an ester carbonyl linkage between the galactopyranose and olefinic moieties (Yang et al. 2003). These data, coupled with the molecular weight information, indicate that this isolate is the C-6" para-hydroxycinnamic acid ester of quercetin-3-β-galactopyranose (FIG. 5).

Interpretation of the NMR spectra obtained on peak 19 ($^1$H reference, COSY, HSQC, HSQCTOCSY, and HMBC) revealed several structurally significant features. The resonances indicating a quercetin backbone were readily observed and assigned by inspection. Resonances consistent with a sugar moiety were also observed. The sugar resonances were somewhat obscured by the residual water in the sample, but several key assignments were possible. The anomeric methine doublet (J=7.6 Hz) was observed at 5.46/101.9 ppm, indicating an axial proton orientation, and therefore a β-linkage to the quercetin backbone. COSY and HSQCTOCSY responses allowed complete, sequential assignment of the sugar ring. A large coupling constant (J=8.3 Hz) was observed for the 2"-3" interaction, indicative of a trans-diaxial interaction, while the 4" proton resonance was observed as a broad singlet. This result requires axial-equatorial interactions for both 3"-4" and 4"-5" and yields the assignment of the sugar moiety as β-galactose.

Another spin system was identified in the aromatic region of the spectrum. This system consisted of an apparent doublet-triplet-triplet pattern in a 2:2:1 ratio and can be readily assigned as a phenyl group (ortho 7.62/129.4; meta 7.26/129.3; para 7.49/133.9 ppm). Investigation of the HMBC data set revealed a 3-bond response between the ortho-protons of this phenyl ring with a carbonyl resonance at 166.1 ppm. A second 3-bond response to this same carbonyl carbon was observed from the 6" methylene protons. Taken with the C-6" chemical shift of 64.9 ppm and the C-9" chemical shift of 129.5 ppm, these data clearly indicate the presence of a benzyl ester moiety at the 6" position of the galactose ring.

The cumulative data showed the presence of mostly glycosylated forms of myricetin and quercetin in Fraction 1 of the 60% methanol Sephadex LH-20 eluate. Together with UV-spectra and peak area percentage these results confirm the identity of peaks 4, 5, 10 and 11 as myricetin-3-α-arabinofuranoside, quercetin-3-β-galactoside, quercetin-3-α-arabinofuranoside and quercetin-3-α-rhamnoside (Puski et al. 1967; Yan et al. 2002). The peaks labeled 1, 8 and 12 correspond to myricetin-3-β-galactoside, quercetin-3-xyloside and 3'-methoxyquercetin-3-β-galactoside (iso-rhamnetin-galactoside), respectively. These components were recently identified in cranberry extracts by Yan et al. (2002), however, the presence of other methyl ethers in cranberries has not been reported. We have fully characterized a second methyl ether derivative in cranberries, 3'-methoxyquercetin-3-α-xylopyranoside (15), and our LC-MS data suggest the presence of a number of other methoxylated flavonols including derivatives of quercetin, myricetin and kaempferol (Table 1).

EXAMPLE 2

Anti-Inflammatory Activity of Sephadex LH-20 Eluate Fractions

The anti-inflammatory activities of different classes of cranberry phenolic compounds separated by Sephadex LH-20 column chromatography were tested in vivo with the 12-O-tetradecanoylphorbol-13-acetate (TPA)-induced mouse ear edema assay described previously (Huang et al. 2003). Each of the treatments was topically applied to both ears of four female CD-1 mice. Treatments included application of either acetone or curcumin controls or the test extract in 20 μl of acetone twenty minutes prior to application of either 5 mg of acetone alone or 1 nmol of TPA in acetone. At five hours post-treatment, mice were sacrificed and 6 mm diameter ear punch biopsies were taken and weighed. Curcumin, a well-known anti-inflammatory agent, was used as a positive control (Chan et al. 1994; Chan 1995). Data were analyzed statistically using ANOVA and the Student-Neuman-Kuels (SNK) multiple means separation test (P<0.05). The ratio of the difference in the weight of ear punches between TPA treated groups receiving pretreatments of acetone and the test extract, respectively, to the difference in the weight of ear punches between acetone pretreated groups subsequently treated with TPA and acetone, respectively, indicates the degree of anti-inflammatory activity of the test extract. Results are summarized in Table 3.

EXAMPLE 3

Anti-Inflammatory Activity of quercetin-3-O-(6"-benzoyl)-β-galactoside

The anti-inflammatory activity of quercetin-3-O-(6"-benzoyl)-β-galactoside (Peak 19) was tested in vivo with the 12-O-tetradecanoylphorbol-13-acetate (TPA)-induced mouse ear edema assay. Each of the treatments was topically applied to both ears of at least five CD-1 female mice. Treatments included application of either acetone or curcumin controls or the test extract in 20 μl of acetone twenty minutes prior to application of 1.5 nmol of TPA in acetone. After 7 hours post-treatment, mice were sacrificed and 6 mm diameter ear punch biopsies were taken and weighed. The ratio of the difference in the weight of ear punches between TPA treated groups receiving pretreatments of acetone and the test extract, respectively, to the difference in the weight of ear punches between acetone pretreated groups subsequently treated with TPA and acetone, respectively, indicates the degree of anti-inflammatory activity of the test extract. Results are summarized in Table 4.

REFERENCES

Avorn, J., Monane, M., Gurwitz, J. H., Glynn, R. J., Choodnovskiy, I., and Lipitz, L. A. Reduction of bacteriuria and Pyuria After Ingestion of Cranberry Juice. *JAMA* 1994, 271(10), 751-754.

Bilyk, A., and Sapers, G. M. Varietal differencies in the quercetin, kaempferol, and myricetin contents of highbush blueberry, cranberry, and thornless blackberry fruits. *J. Agric. Food Chem.* 1986, 34, 585-588.

Chan M. M., and Fong, D. Anti-inflammatory and cancer preventive immunomodulation through diet: The effects of curcumin on T lymphocyte response. In "Food Phytochemicals for Cancer Prevention II", Ho, C. T., Osawa, T., Huang, M. T., Rosen, R. T. (Eds.) American Chemical Society, Washington DC, 1994, 222-230.

Chan M. M. Inhibition of tumor necrosis factor by curcumin, a phytochemical. *Biochem. Pharmacol.* 1995, 49, 1551-1556.

Cunningham, D. G., Vannozzi, S., O'Shea, E., and Turk, R. Analysis and standardization of cranberry products. In Quality Management of Nutraceuticals, Eds. Ho, C., and Zheng, Q. Y. ACS, Washington D.C. ACS Symposium Series 803. 2002, 152-167.

Foo, L. Y., and Porter, L. J. The structure of tannins of some edible fruits. *J. Sci. Food Agric.* 1981, 32, 711-716.

Foo, L. Y., Lu, Y., Howell, A. B., and Vorsa, N. The structure of cranberry proanthocyanidins which inhibit adherence of uropathogenic P-fimbriated *Escherichia coli* in vitro. *Phytochemistry* 2000a, 5, 173-181.

Foo, L. Y., Lu, Y., Howell, A. B., and Vorsa, N. A-type proanthocyanidin trimers from cranberry that inhibit adherence of uropathogenic P-fimbriated *Escherichia coli*. *J. Nat Prod*. 2000b, 63, 1225-1228.

Formica, J. V., and Regelson, W. Review of the biology of quercetin and related bioflavonoids. *Fd. Chem. Toxic*. 1995, 33, 1061-1080.

Fukushi, Y., Orikasa, S., and Kagayama, M. An electron microscopic study of the interaction between vesical epithelium and *E. coli*, Invest. Urol. 1979, 17, 61-68.

Hakkinen S. H., Karenlampi, S. O., Heinonen, M., Mykkanen, H. M., and Torronen, A. R. Content of the flavonols quercetin, myricetin, and kaempferol in 25 edible berries. *J. Agric.Food Chem*. 1999, 47, 2274-2279.

Heimhuber, B., Wray, V., Galensa, R., and Herrmann, K. Benzoylglucoses from two Vaccinium species. *Phytochemistry* 1990, 29, 2726-2727.

Held, P. J., Hanno, P. M., and Wein, A. J. Epidemiology of interstitial cystitis. In "Interstitial cystitis", Hanno, P. M., Staskin, D. R., and Krane, R. J. (Eds.), Springer-Verlag, London, England, 1990, 7-15.

Hollman, P. C., de Vries, J. H., van Leeuwen, S. D., Mengelers, M. J., and Katan, M. B. Absorption of dietary quercetin glycosides and quercetin in healthy ileostomy volunteers. *Am. J Clin. Nutr*. 1995, 62, 1276-1282.

Hollman, P. C., Buijsman, M. N., van Gameren, Y., Cnossen, E. P., de Vries, J. H., and Katan, M. B. The sugar moeity is a major determinant of the absorption of dietary flavonoid glycosides in man. *Free Radic. Res*. 1999, 31, 569-573.

Hong, V., and Wrolstad, R. E. Cranberry juice composition. *J. Assoc. Off. Anal. Chem*. 1986, 69,199-207.

Hong, V., and Wrolstad, R. E. Use of HPLC separation/ photodiode array detection for characterization of anthocyanins. *J. Agr. Food Chem*. 1990, 38, 708-715.

Huang, M.-T.; Liu, Y., Xie, J.-G., Newmark, H. H., and Ho, C.-T. Protective effect of dibenzoylmethane on chemically- and UV light-induced skin inflammation, sunburn lesions, and skin carcinogenesis in mice. ACS Symposium Series, 2003, 851 (Food Factors in Health Promotion and Disease Prevention), 196-207.

Jin, C., Strembiski, W., Kulchytska, Y., Micetich, R. G., and Daneshtalab, M. Flavonoid glycosides from *Ledum palustre* L.subsp.decumbens (Ait) Hulton. Daru, Journal of Faculty of Pharmacy, Tehran University of Medical Sciences. 1999, 7, 5-8.

Kawada, N., Seki, S., Inoue, M., and Kuroki, T. Effect of antioxidants, resveratrol, quercetin, and N-acetylcysteine, on the functions of cultured rat hepatic stellate cells and Kupffer cells. Hepatology 1998, 27, 1265-1274.

Mabry, T. J., Markham, K. R., and Thomas, M. B. The systematic identification of flavonoids. Springer-Verlag: New York, 1970, 128-130.

Machiex, J. J., Fleuriet, A., and Billot, J. Fruit phenolics. CRC Press: Boca Raton, Fla., 1990.

Martinez, J. J., Mulvey, M. A., Schilling, J., Pinker, J., and Hultgren, S. Type 1 pilus-mediated bacterial invasion of bladder epithelial cells. *EMBO J* 2000, 9, 2803-2812.

Marwan, A. G., and Nagel, C. W. Identification of the hydroxycinnamic acid derivatives in cranberries. *J. Food Sci*. 1982, 47, 774-782.

McTaggart, L. A., Rigby, R. C., and Elliot, T. S. J. The pathogenesis of urinary tract infections associated with *Escherichia coli*, *Staphylococcus saprophyticus* and *S. epidermidis*. *J. Med. Microbiol*. 1990, 32, 135-141.

Mulvey, M. A., Lopez-Boado, Y. S., Wilson, C. L., Roth, R., Parks, W. C., Heuser, J., and Hultgren, S. J. Induction and evasion of host defenses by type 1-piliated uropathogenic *Escherichia coli*. *Science* 1998, 282, 1494-1497.

Mulvey, M. A., Schilling, J. D., and Hultgren, S. J. The establishment of a persistent *E. coli* reservoir during the acute phase of a bladder infection. *Infection and Immunity* 2001, 69, 4572-4579.

Puski, G., and Francis, F. Flavonol glycosides in cranberries. *J. Food Sci*. 1967, 32, 527-530.

Schilling, J. D., Mulvey, M. A., Vincent, C. D., Lorenz, R. G., and Hultgren, S. J. Bacterial invasion augments epithelial cytokine responses to *Escherichia coli* through a lipopolysaccharide-dependent mechanism. *J. Immunol*. 2001, 166, 1148-1155.

Schmidt and Sobota An examination of the anti-adherence activity of cranberry juice on urinary and nonurinary bacterial isolates. *Microbios*. 1988, 55, 173-181.

Sobota Inhibiton of bacterial adherence by cranberry juice: Potential use for the treatment of urinary tract infections. *J. Urol*. 1984, 131, 1013-1016.

Sun, J., Chu, Y., Wu, X., and Liu, R. H. Antioxidant and antiproliferative activities of common fruits. *J. Agric. Food Chem*. 2002, 50, 7449-7454.

Vera, J. C. Reyes, A. M., Velasquez, F. V., Rivas, C. I., Zhang, R. H., Strobel, P., Slebe, J. C., Nunez-Alarcon, J., and Golde, D. W. Direct inhibition of the hexose transporter GLUT1 by tyrosine kinase inhibitors. *Biochem*. 2001, 40, 777-790.

Vinson, J. A., Su, X., Zubik, L., and Bose, P. Phenol antioxidant quantity in foods: fruits. *J. Agric. Food Chem*. 2001, 49, 5315-5321.

Vlahos, C. J., Matter, W. F., Hui, K. Y., and Brown, R. F. A specific inhibitor of phosphatidylinositol 3-kinase, 2-(4-morpholinyl)-8-phenyl-4H-1-benzopyran-4-one (LY294002). *J. Biochem. Chem*. 1994, 269, 5241-5248.

Wadsworth, T. L., and Koop, D. R. Effects of the wine polyphenolics quercetin and resveratrol on pro-inflammatory cytokine expression in RAW 264.7 macrophages. *Biochem. Pharm*. 1999, 57, 941-949.

Woffram, S., Block, M., and Ader, P. Quercetin-3-glucoside is transported by the glucose carrier SGLT1 across the brush border membrane of the rat small intestine. *J. Nutr*. 2002, 132, 630-635.

Xagorari, A., Papapetropoulos, A., Mauromatis, A., Economou, M., Fotsis, T., and Roussos, C. Luteolin inhibits endotoxin-stimulated phosphorylation cascade and proinflammatory cytokine production in macrophages. *JPET* 2001, 296, 181-187.

Yan X., Murphy B. T., Hammond, G. B., Vinson, J. A., and Neto, C. C. Antioxidant activities and antitumor screening of extracts from cranberry fruit (*Vaccinium macrocarpon*). *J. Agric. Food Chem*. 2002, 50, 5844-5849.

Yang, S. T., Gard, J. K, Harrigan, G., Parnas, B., Likos, J., and Crouch, R. Increasing spectral information with shorter acquisitions: the advantages of using F-1 selection in structural determinations. *Mag. Reson. Chem*. 2003, 41, 42-48.

Zafriri, D., Ofek, I., Adar, R., Pocino, M., and Sharon, N. Inhibitory activity of cranberry juice on adherence of type 1 and type P fimbriated *Escherichia coli* to eucaryotic cells. *Antimicrobial Agents and Chemotherapy* 1989, 1, 92-98.

Zheng, Z., and Shetty, K. Solid-state bioconversion of phenolics from cranberry pomace and role of Lentinus edodes β-glucosidase. *J. Agric. Food Chem*. 2000, 48, 895-900.

Zuo, Y., Wang, C., and Zhan J. Separation, characterization, quantitation of benzoic and phenolic antioxidants in American cranberry fruit by GC-MS. *J. Agric. Food Chem.* 2002, 50, 3789-3794.

We claim:

1. An isolated compound having the formula as shown, including pharmaceutically acceptable salts thereof:

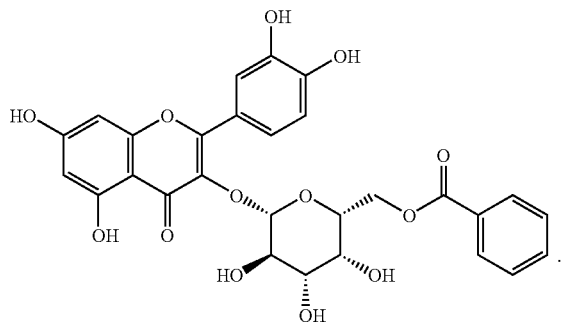

2. A method to obtain the compound of claim 1 from cranberries, the method comprising processing the cranberries to obtain a cranberry preparation having a solids content of at least 50% Brix and isolating the compound of claim 1 from the cranberry preparation.

3. A method for the treatment of an inflammatory condition comprising administering a therapeutically effective dose of the compound of claim 1, including pharmaceutically acceptable salts thereof.

4. A pharmaceutical composition comprising a pharmaceutically acceptable carrier in admixture with the compound of claim 1, wherein the composition is substantially free of anthocyanins and proanthocyanidins.

5. A method for the treatment of an inflammatory condition comprising administering a therapeutically effective dose of the pharmaceutical composition of claim 4.

6. A dietary supplement composition comprising a consumable carrier in admixture with the compound of claim 1, wherein the composition is substantially free of anthocyanins and proanthocyanidins.

7. A method for the treatment of an inflammatory condition comprising administering a therapeutically effective dose of the dietary supplement composition of claim 6.

8. A food composition comprising a consumable carrier in admixture with the isolated compound of claim 1.

9. A method for the treatment of an inflammatory condition comprising administering a therapeutically effective dose of the food composition of claim 8.

10. The food composition of claim 8 wherein the consumable carrier is a cranberry-containing food product.

11. The food composition of claim 10 wherein the cranberry-containing food product is a dried cranberry, a sweetened and dried cranberry, a powered cranberry, a flavored fruit piece, a sauce, a jelly, a relish, a juice, a wine or a cranberry juice-containing product.

12. The food composition of claim 8 wherein the consumable carrier is a beverage.

13. A cosmetic composition comprising a cosmetically acceptable carrier in admixture with the compound of claim 1.

14. A method for the treatment of an inflammatory condition comprising administering a therapeutically effective dose of the cosmetic composition of claim 13.

15. The method of claim 3, wherein the inflammatory condition is urinary tract inflammation.

16. The method of claim 3, wherein the inflammatory condition is cystitis.

17. The method of claim 5, wherein the inflammatory condition is urinary tract inflammation.

18. The method of claim 5, wherein the inflammatory condition is cystitis.

19. The method of claim 7, wherein the inflammatory condition is urinary tract inflammation.

20. The method of claim 7, wherein the inflammatory condition is cystitis.

21. The method of claim 9, wherein the inflammatory condition is urinary tract inflammation.

22. The method of claim 9, wherein the inflammatory condition is cystitis.

23. A pharmaceutical composition consisting essentially of the compound of claim 1 and a pharmaceutically acceptable carrier.

24. A dietary supplement composition consisting essentially of the compound of claim 1 and a consumable carrier.

* * * * *